(12) United States Patent
Müller et al.

(10) Patent No.: US 6,383,584 B2
(45) Date of Patent: *May 7, 2002

(54) AZLACTONE-DERIVATIZED POLYAMIDES

(75) Inventors: Egbert Müller, Erzhausen; Anja Seiler, Gross-Zimmern, both of (DE)

(73) Assignee: Merck Patent Gesellschaft mit beschrankter (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/214,381
(22) PCT Filed: Jun. 24, 1997
(86) PCT No.: PCT/EP97/03300
§ 371 Date: Jan. 6, 1999
§ 102(e) Date: Jan. 6, 1999
(87) PCT Pub. No.: WO98/01496
PCT Pub. Date: Jan. 15, 1998

(30) Foreign Application Priority Data

Jul. 6, 1996 (DE) .......................... 196 27 302

(51) Int. Cl.$^7$ .............................................. B29C 71/00
(52) U.S. Cl. .................... 428/35.7; 428/36.8; 428/36.9; 428/304.4; 428/395; 428/36.5; 428/308.4; 428/311.5; 428/313.5; 428/361; 428/376; 427/212; 525/426
(58) Field of Search ......................... 525/426; 428/35.7, 428/36.8, 36.9, 304.4, 395, 36.5, 308.4, 311.5, 313.5, 361, 376; 427/212

(56) References Cited

U.S. PATENT DOCUMENTS

| | | | |
|---|---|---|---|
| 4,737,560 A | | 4/1988 | Heilmann et al. .......... 526/304 |
| 5,408,002 A | | 4/1995 | Coleman et al. ............. 525/204 |
| 5,451,453 A | * | 9/1995 | Gagnon et al. .......... 428/305.5 |
| 5,866,673 A | * | 2/1999 | Müller et al. ............... 528/310 |
| 5,993,935 A | * | 11/1999 | Rasmussen et al. ........ 428/120 |

FOREIGN PATENT DOCUMENTS

EP    0 392 783    10/1990

* cited by examiner

*Primary Examiner*—Ana Woodward
(74) *Attorney, Agent, or Firm*—Millen, White, Zelano & Branigan, P.C.

(57) ABSTRACT

The present invention relates to an azlactone-derivatized polyamide shaped article made by reacting at least one polyamide with a solution comprising an aza-bicyclo compound and a vinylazlactone derivative of the formula I

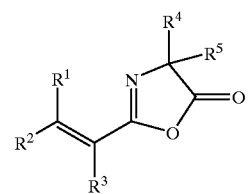

wherein $R^1$, $R^2$, $R^3$, $R^4$, and $R^5$ are defined herein.

11 Claims, No Drawings

AZLACTONE-DERIVATIZED POLYAMIDES

The invention relates to azlactone-derivatized polyamides, to shaped articles comprising azlactone-derivatized polyamides, and to processes for their preparation.

Azlactone-derivatized carrier materials are known from the literature; for example, U.S. Pat. No. 4,737,560 discloses crosslinked carrier materials which comprise azlactone groups. EP 0 392 783 discloses processes for the graft polymerization of substrate polymers, where the grafted-on side chains comprise aclactone [sic] groups. These carrier materials are suitable for binding proteins insofar as the azlactone groups are sufficiently accessible to compounds of high molecular mass. Porous membranes of polyamides exhibit outstanding flow properties; membranes of polyamides can also be produced with pores whose internal surfaces are readily accessible to compounds of high molecular mass. Polyamides, moreover, exhibit low levels of nonspecific binding with respect to proteins.

The patent application DE 195 01 726.9 (WO 96/22 316) discloses derivatized polyamide membranes which are in the form of block polymers. The monomers polymerized on can also be reacted to form azlactone groups. The preparation of these azlactone-containing polyamide membranes is relatively complex, since first of all it is necessary to prepare a polymerizable derivative of the polyamide and then the block polymer has to be prepared, with the monomers used in its preparation including precursor compounds for the azlactone group. Finally, the precursor compounds must be converted into the azlactone group. The object is therefore to provide a simplified process for preparing azlactone-derivatized polyamides.

It has been found that amino groups, which are usually present terminally in polyamides, can be reacted with vinylazlactone derivatives, the vinyl group reacting with the amino group to produce, in a simple manner, an azlactone-derivatized polyamide. Since the azlactone group is known to react with amino groups, this reaction possibility is unexpected. Where the polyamides used as the substrate polymer contain carboxyl groups, these carboxyl groups can first of all be reacted with diamino compounds by the process disclosed in DE 196 24 813.2 (PCT/EP97/02 768) to provide additional amino groups.

The invention provides azlactone-derivatized polyamides obtainable by reacting polyamides with a solution comprising an azabicyclo compound and a vinylazlactone derivative of the formula I

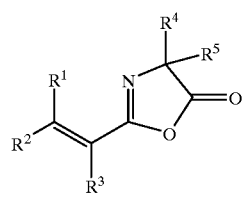

in which
R$^1$, R$^2$ and R$^3$ independently of one another denote H or CH$_3$;
R$^4$ and R$^5$ independently of one another denote H or C$_1$- to C$_5$-alkyl.
Preferably, R$^1$, R$^2$ and R$^3$ are H and R$^4$ and R$^5$ are methyl.

The invention provides for the use of the azlactone-derivatized polyamides for the binding of amino-containing compounds. Examples of suitable amino-containing compounds are proteins, including enzymes and antibodies.

The invention provides separation materials obtained by reacting an azlactone-derivatized polyamide of the invention with an amino-containing separation effector. Examples of suitable amino-containing separation effectors are antibodies and other affinity ligands for affinity chromatography. Other separation effectors are known to the person skilled in the art.

The invention provides immobilized enzymes obtainable by reacting an azlactone-derivatized polyamide of the invention with an enzyme.

Polyamides suitable as the base polymer are known to the person skilled in the art and are also obtainable commercially. They include, for example, the polymers known under the trade name NYLON®, e.g. NYLON® 66 and NYLON® 6. Porous or nonporous shaped articles consisting of such polyamides are likewise known and are also obtainable commercially; they include, for example, bead-shaped articles, membranes, hoses, hollow fiber membranes, and sponges. The reaction of such shaped articles is preferred, since under the reaction conditions as used in DE 195 01 726.9 and DE 196 24 813.2 (reaction temperature below 80° C.) their shape is retained whereas other processes for derivatizing polyamide are performed in the melt or in solution.

The reaction sequence of the invention is preferably performed at between 0 and 70° C., in particular at between 10 and 60° C.; that is, at temperatures below the melting point of the starting polyamide. Since the starting polyamide need not be dissolved, the reaction sequence of the invention can preferentially also be applied to polyamide mouldings without any notable change in their form. The reaction is catalyzed by azabicyclo compounds, examples being 1,8-diazabicyclo-[5.4.0]undec-7-ene (DBU), 1,5-diazabicyclo[4.3.0]non-5-ene (DBN) and 1,5,7-triazabicyclo[4.4.0]dec-5-ene (TBD). The vinylazlactone derivative is dissolved together with the catalyst in a solvent which is inert to the azlactone derivative. Preferred solvents are those which do not attack the polyamide; examples are dimethylformamide (DMF) and dimethyl sulfoxide (DMSO).

Even without further statements it is assumed that a person skilled in the art will be able to utilize the above description in the widest scope. The preferred embodiments are therefore to be interpreted merely as a descriptive disclosure which in no way has any limiting nature whatsoever.

The complete disclosure content of all above- and below-mentioned applications, patents and publications, and of the corresponding application(s) DE 196 27 302.1, filed on Jun. 7, 1996, are hereby incorporated by reference into this application.

EXAMPLES

The examples which follow are intended to illustrate the invention and do not constitute any restriction of the invention.

In the text below, room temperature means a temperature of between 15 and 30° C.

Example 1

Reacting a Polyamide Hollow Fiber Membrane With Vinyldimethylazlactone 2.56 g of 1,8-diazabicyclo[5.4.0]undec-7-ene (DBU) and 32 ml of vinyldimethylazlactone are dissolved in 160 ml of dimethylformamide. A polyamide hollow fiber bundle (polyamide 6, 64 filaments; individual fiber diameter; internal 0.2 mm, external 0.5 mm; average pore width 0.5 μm) is packed into a 300-10 mm SUPERFORMANCE® chromatography column (from E. Merck) and the above solution is pumped in circulation at room temperature and with a flow rate of 2 ml/min through the hollow fiber bundle for 24 hours. Subsequently, the derivatized hollow fiber bundle is rinsed with dimethylformamide, acetone, ethyl acetate and acetone and is dried in a vacuum drying cabinet at 50° C.

Example 2

Binding γ-Globulin to a Vinyldimethyl-Azlactone-Activated Polyamide Hollow Fiber Membrane 1 g of γ-globulin is dissolved in 100 ml of Tris buffer (50 mM, pH 7.4) and this solution is pumped in circulation at room temperature through the hollow fiber bundle derivatized in accordance with Example 1 (flow rate: 5 ml/min). During this procedure, the protein concentration in the solution and its decrease were determined continuously by means of UV spectrophotometry; after two hours, the protein concentration in the pump-circulated solution remained constant. After washing out the hollow fiber bundle with Tris buffer (50 mM, pH 7.4) and 0.1 M acetic acid, the amount of protein covalently bound in the hollow fiber bundle was determined as 66.5 mg.

A hollow fiber module with a polyamide membrane coated with γ-globulin as described above can be used for affinity chromatography, for the binding of anti-γ-globulin antibodies.

Example 3

Reacting A Polyamide With Ethylenediamine

To carry out the synthesis a polyamide hollow fiber bundle made from polyamide 6 is packed in a 300-10 mm SUPERFORMANCE® chromatography column (from E. Merck). An inert pump is attached to this column. For the reaction, 10 mol of ethylene diamine and 0.2 mol of 1-ethyl-3-(3-dimethylaminopropyl)carbodiimide (EDC) are dissolved in 200 ml of 0.1 M sodium acetate buffer (pH 4.7) and pumped in circulation at a fast rate (5 ml/min) at room temperature for 5 hours. Subsequently, the derivatized membrane is washed to neutrality with 1 M phosphate buffer pH 7 and with water.

Example 4

Reacting A Polyamide Hollow Fiber Membrane With Vinyldimethylazlactone

The reaction of the polyamide amino-modified in accordance with Example 3 is performed as described in Example 1.

What is claimed is:

1. An azlactone-derivatized polyamide shaped article made by reacting at least one polyamide shaped article with a solution comprising a catalytically effective amount of an aza-bicyclo compound and a vinylazlactone of the formula I

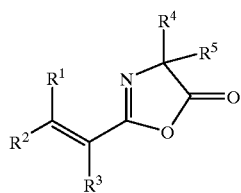

in which
$R^1$, $R^2$ and $R^3$ independently of one another denote H or $CH_3$;
$R^4$ and $R^5$ independently of one another denote H or $C_1$- to $C_5$-alkyl.

2. An azlactone-derivatized polyamide shaped article according to claim 1, wherein carboxyl groups of the polyamide are reacted with a diamino compound prior to the reaction with the vinylazlactone of the formula I.

3. An azlactone-derivatized polyamide shaped article according to claim 2, which is porous.

4. An azlactone-derivatized polyamide shaped article according to claim 1, which is porous.

5. An azlactone-derivatized polyamide shaped article according to claim 1 wherein only one azlactone radical from the compound of formula I is attached to each polyamide reaction site.

6. An azlactone-derivatized polyamide shaped article according to claim 1, which is a bead, a membrane, a hose, a hollow fiber, or a sponge.

7. An azlactone-derivatized polyamide shaped article according to claim 1 wherein
$R^1$, $R^2$, and $R^3$ are H and $R^4$ and $R^5$ are methyl.

8. An azlactone-derivatized polyamide shaped article according to claim 1, wherein the azlactone-derivatized polyamide shaped article is only surface-modified by the catalytically effective amount of an aza-bicyclo compound and a vinylazlactone.

9. A method of binding an amino-containing compound comprising contacting at least one amino-containing compound with the azlactone-derivatized polyamide shaped article of claim 1.

10. A process for making an azlactone-derivatized polyamide shaped article comprising:
reacting under basic conditions a polyamide shaped article with a solution comprising a catalytically effective amount of an azabicyclo compound and a vinylazlactone of formula I

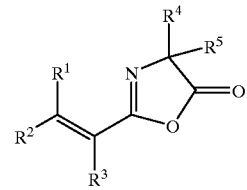

in which
$R^1$, $R^2$ and $R^3$ independently of one another denote H or $CH_3$;
$R^4$ and $R^5$ independently of one another denote H or $C_1$- to $C_5$-alkyl;
wherein only one azlactone radical from the compound of formula I is attached to each polyamide reaction site.

11. An azlactone-derivatized polyamide shaped article made by surface-modifying at least one polyamide shaped article with a solution comprising a catalytically effective amount of an aza-bicyclo compound and a vinylazlactone of the formula I

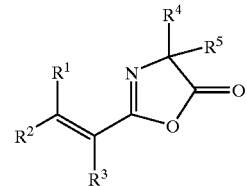

wherein
$R^1$, $R^2$ and $R^3$ independently of one another denote H or $CH_3$;
$R^4$ and $R^5$ independently of one another denote H or $C_1$- to $C_5$-alkyl; and only one azlactone radical from the compound of formula I is attached to each polyamide reaction site.

* * * * *